United States Patent
Giannini et al.

(10) Patent No.: US 10,300,035 B2
(45) Date of Patent: May 28, 2019

(54) HOMOGENEOUS FORMULATION COMPRISING OMEGA-3 POLYUNSATURED FATTY ACID AND RESVERATROL FOR ORAL ADMINISTRATION

(71) Applicant: ALFASIGMA S.P.A., Milano, MI (US)

(72) Inventors: Giuseppe Giannini, Pomezia (IT); Mosè Santaniello, Pomezia (IT)

(73) Assignee: ALFASIGMA S.P.A., Bologna (IT)

( * ) Notice: Subject to any disclaimer, the term of this patent is extended or adjusted under 35 U.S.C. 154(b) by 90 days.

(21) Appl. No.: 15/316,151

(22) PCT Filed: Mar. 26, 2015

(86) PCT No.: PCT/EP2015/056524
§ 371 (c)(1),
(2) Date: Dec. 2, 2016

(87) PCT Pub. No.: WO2015/185238
PCT Pub. Date: Dec. 10, 2015

(65) Prior Publication Data
US 2017/0119720 A1    May 4, 2017

(30) Foreign Application Priority Data
Jun. 4, 2014    (EP) .................................. 14001941

(51) Int. Cl.
| | |
|---|---|
| *A61K 9/00* | (2006.01) |
| *A61K 9/08* | (2006.01) |
| *A61K 9/48* | (2006.01) |
| *A61K 31/05* | (2006.01) |
| *A61K 45/06* | (2006.01) |
| *A61K 47/12* | (2006.01) |
| *A61K 47/24* | (2006.01) |
| *A61K 31/232* | (2006.01) |

(52) U.S. Cl.
CPC .......... *A61K 31/232* (2013.01); *A61K 9/0053* (2013.01); *A61K 9/08* (2013.01); *A61K 9/4891* (2013.01); *A61K 31/05* (2013.01); *A61K 45/06* (2013.01); *A61K 47/12* (2013.01); *A61K 47/24* (2013.01)

(58) Field of Classification Search
None
See application file for complete search history.

(56) References Cited

FOREIGN PATENT DOCUMENTS

| | | | |
|---|---|---|---|
| WO | 01/26666 A2 | 4/2001 | |
| WO | WO-0126666 A2 * | 4/2001 | ............. A61K 36/16 |
| WO | 2011/162802 A1 | 12/2011 | |
| WO | 2013/171204 A2 | 11/2013 | |
| WO | 2014/0095628 A1 | 6/2014 | |

OTHER PUBLICATIONS

Stuchlík et al. "Lipid-based vehicle for oral drug delivery", Biomed. Papers, 145(2), 2001, pp. 17-26. (Year: 2001).*
International Search Report issued in PCT/EP2015/056524 dated May 28, 2015 (3 pages).
Written Opinion issued in PCT/EP2015/056524 dated May 28, 2015 (7 pages).

* cited by examiner

*Primary Examiner* — Melissa L Fisher
(74) *Attorney, Agent, or Firm* — Silvia Salvadori, P.C.; Silvia Salvadori

(57) ABSTRACT

The present invention relates to homogeneous formulations comprising omega-3 polyunsaturated fatty acids (n-3 PUFA) and resveratrol for oral administration, in which the resveratrol is solubilized in a solvent system consisting of omega-3 polyunsaturated fatty acids (n-3 PUFA), or their alkyl esters, and a ionic emulsifier. The composition according to the present invention can be formulated as food or nutritional supplement or medicament in the prevention or treatment of cardiovascular diseases due to lipid metabolism disorders and increased platelets aggregation, as well as damages due to free radicals and/or viral diseases.

16 Claims, No Drawings

HOMOGENEOUS FORMULATION COMPRISING OMEGA-3 POLYUNSATURED FATTY ACID AND RESVERATROL FOR ORAL ADMINISTRATION

RELATED APPLICATIONS

This application is filed under 35 U.S.C. § 371 as the U.S. national phase of International Application PCT/EP2015/056524, filed Mar. 26, 2015, which designated the U.S. and claims priority to European Application No. 14001941.5, filed Jun. 4, 2014. The entire disclosure of both applications, including any drawings, is hereby incorporated herein by reference.

FIELD OF THE INVENTION

The present invention relates to homogeneous formulations comprising omega-3 polyunsaturated fatty acids (n-3 PUFA) and resveratrol for oral administration, in which resveratrol is solubilized in a solvent system consisting of omega-3 polyunsaturated fatty acids (n-3 PUFA) or alkyl esters thereof, and a ionic emulsifier.

In particular, the present invention relates to the homogeneous formulations mentioned above, for use in the prevention or treatment of cardiovascular diseases due to lipid metabolism disorders and increased platelets aggregation, as well as damages due to free radicals and/or viral diseases.

BACKGROUND OF THE INVENTION

Cardiovascular diseases related to abnormal lipid metabolism are very frequent in industrialised countries. In Italy, for instance, according to the data from the World Health Organization published on April 2011, the number of decreases in Italy for cardiovascular diseases reached 18.65% of the overall mortality. Our knowledge of the relationships between cholesterol and coronary heart disease stem from epidemiological studies conducted over the past few years. The conclusions reached in these studies indicate that the development of severe coronary atherosclerosis and coronary heart disease are closely correlated with serum cholesterol levels (Breuer, H. W. M.; European Cardiology, 2005; 1-6).

Platelets play an important, but often under-recognized role in cardiovascular disease. For example, the normal response of the platelet can be altered, either by increased pro-aggregatory stimuli or by diminished anti-aggregatory substances to produce conditions of increased platelet activation/aggregation occurring in cardiovascular disease states both on a chronic (e.g. stable angina pectoris) and acute basis (e.g. acute myocardial infarction). In addition, platelet hyperaggregability is also associated with risk factors of coronary artery disease (e.g. smoking, hypertension, and hypercholesterolemia). Finally, the utility of an increasing range of anti-platelet therapies in the management of the above disease states further emphasizes the pivotal role platelets play in the pathogenesis of cardiovascular disease. A recently published paper provides a comprehensive overview of the normal physiologic role of platelets in maintain homeostasis, the pathophysiologic processes that contribute to platelet dysfunction in cardiovascular disease and the associated role and benefits of anti-platelet therapies (Kottke-Marchant K.: Cleveland Clinic Journal of Medicine; 2009 April; 76(1): 1-7).

Evidence is accumulating that most of the degenerative diseases that afflict humanity have their origin in deleterious free radical reactions. These diseases include atherosclerosis, cancer, inflammatory joint disease, asthma, diabetes, senile dementia and degenerative eye disease. The process of biological ageing might also have a free radical basis. Most free radical damage to cells involves oxygen free radicals or, more generally, activated oxygen species (AOS) which include non-radical species such as singlet oxygen and hydrogen peroxide as well as free radicals. The AOS can damage genetic material, cause lipid peroxidation in cell membranes, and inactivate membrane-bound enzymes. Antioxidant supplementation of our diet is needed to ensure a more healthy elderly population (Aust N Z J Ophthalmol. 1995 February; 23(1):3-7).

Omega-3 polyunsaturated fatty acids (n-3 PUFA) have demonstrated a beneficial effect in the prevention of cardiovascular events (Aarsetoey H. et al.; Cardiology Research and Practice, Volume 2012: 1-16), possibly by means of an antiinflammatory, antithrombotic and antiarrhythmic mechanism (Sethi S. et al.; Blood 2002:100:-1340-6; Billman G E, et al.; Circulation 3 1999: 99:2452-7). The hypolipidic effect was the first detected, so at first these drugs had been used for the treatment of dislipidemic disorders, while the antiinflammatory, antithrombotic, antiatherosclerotic and antiarrhythmogenic effects have been found later. GISSI-Prevention trial (Lancet 1999 354: 447-55) was the first trial demonstrating the efficacy and tolerability of n-3 PUFAs in post-myocardial infarction patients. According to the evidence in literature, today n-3 PUFAs are indicated for the primary and secondary prevention of ischemic cardiopathy and sudden cardiac death (SCD) (Mori T A, Beilin L J. Long-chain omega-3 fatty acids, blood lipids and cardiovascular risk reduction. Curr. Opin. Lipidol. 2001; 12:11-7). In Nutrition and Dietary Supplements 2011 September 14; 93-100 it is described the role of n-3 series polyunsaturated fatty acids in cardiovascular disease prevention.

Resveratrol (trans-3,4',5,-trihydroxystilbene) is a polyphenol molecule located in the skins of black grapes. It is known that it has cardioprotective effects, acting as inhibitor of platelet aggregation (Szmitko P E, et al. *Circulation* January 2005, 111 (2) p 10-11; Das D K, et al. "Resveratrol in cardioprotection: a therapeutic promise of alternative medicine"; *Mol. Interv.*, 2006, 6 (1): 36-47). It also acts as antioxidant and skin protecting agent (Afaq, Farrukh et al. "Botanical antioxidants in the prevention of photocarcinogenesis and photoaging"; *Experimental Dermatology*, 2006, 15 (9): 678-84). Resveratrol has been intensively studied recently, in relation to the known beneficial properties of red wine, of which it is one of the fundamental ingredients (*Life Sci.*, 71, 2145-52, 2002). Numerous studies have demonstrated an anticarcinogenic activity of resveratrol, whose mechanisms of action of which can be subdivided as follows: inhibition of activation of transcription factor NF-kB, capable of regulating the expression of various genes involved in inflammatory and carcinogenic processes (*Lancet*, 341, 1103-1104, 1993; *Science*, 275, 218.220, 1997; *Proc. Natl. Acad. Sc.*, 94, 14138-14143, 1997; *Life Science*, 61, 2103-2110, 1997; *Brit. J. Pharm.*, 126, 673-680, 1999; *J. Imm.*, 164, 6509-6519, 2000); inhibition of various proteins, including protein kinase C (Stewart, J. R., Ward, N. E., loannides, C. G. and O'Brian, C. A., *Resveratrol preferentially inhibits protein kinase C-catalyzed phosphorylation of a cofactor-independent, arginine-rich protein substrate by a novel mechanism, Biochemistry.* 1999, 38, 13244-13251), ribonucleotide reductase (*FEBS Lett.*, 421, 277-279, 1998) and cyclo-oxygenase-2 (COX-2) in mammalian epithelial cells (Steinmetz K L, Tyson C K, Meierhenry E F, Spalding J W, Mirsalis J C. *Examination of genotoxicity, toxicity and morphologic alterations in hepatocytes following in vivo or in vitro exposure to methapyrilene. Carcinogenesis.* 1988 June; 9(6):959-963)); activation of caspases 2, 3, 6 and 9 (*FASEB J.,* 1613-1615, 2000) and modulation of the gene p53, which is a known tumour suppressor (Soleas G J, Goldberg D M, Grass L, Levesque M, Diamandis E P. *Do wine polyphenols modulate p53 gene expression in human cancer cell lines? Clin Biochem* 2001; 34: 415-420).

In Free Radic. Res., 33, 105-114, 2000 it is described the antioxidant activity of resveratrol and its ability to counteract the damaging effects produced by various substances and/or conditions that cause intracellular oxidative stress.

In EP1567137B1 it is described the use of resveratrol for treating influenza virus infections.

WO 2011161501 describes solid compositions in form of powders or granulates wherein the active ingredient is insoluble or poorly soluble in water and/or thermolabile and/or having unpleasant organoleptic properties. The method described is a dispersion in a lipid matrix containing a triglyceride, a polyoxyethylene sorbitan ester and ascorbyl palmitate.

Patent application WO 2011120530 discloses solid porous inert carrier compositions comprising a porous silicium dioxide (silicon dioxide) and a release enhancing agent that can be loaded with pharmaceutical oils, among which fish oil. An example of preparation of compositions comprising n-3 PUFA in combination with one or more active ingredients is described in EP2517697. In particular, are described microcapsule suspensions comprising one or more statins in alkyl esters of n-3 PUFA, in which the statins are isolated from contact with the alkyl ester of n-3 PUFA by means of a polymeric membrane that can be easily disintegrated in the gastrointestinal medium.

Most of the methods known in the art, useful for preparing compositions containing resveratrol and n-3 PUFA, include microencapsulation or coating processes which are long and expensive. These studies are focused on finding suitable delivery methods of resveratrol in a single dose within an oily phase.

In the art methods for the solubilization of resveratrol in n-3 PUFA are not known.

Resveratrol, in fact, while keeping very good qualities as stabilizing agent in the prevention or reduction of the n-3 PUFA degradation, is almost insoluble in most of the oil phases used in the protocols for the preparation of medicines and nutraceuticals. Even the addition of certain emulsifiers and/or cosurfactant is not effective in achieving the desired purpose.

Considering the advantages of resveratrol in combination with n-3 PUFA fatty acids for medical or nutraceutical use, it becomes more and more noticeable the need to find an efficient method for solubilizing resveratrol in the oil phase.

DESCRIPTION OF THE INVENTION

It has now surprisingly been found that using a solvent system, consisting of an ionic emulsifier (a deoiled phosphatidylcholine-enriched lecithin) and omega-3 polyunsaturated fatty acid (n-3 PUFA), it's now possible to obtain a complete solubilization of significant amount of resveratrol in said solvent system.

It is therefore an object of the present invention a composition which comprises:
(1) a solvent system consisting of:
omega-3 polyunsaturated fatty acid or alkyl esters thereof;
an ionic emulsifier selected from the group consisting of deoiled phosphatidylcholine-enriched lecithin; or deoiled phosphatidylcholine-enriched lecithin wherein said phosphatidylcholine is present in an amount greater than 92%, or Epikuron™ 200; and
(2) resveratrol, or a natural extract containing resveratrol;
in which resveratrol is completely dissolved in the solvent system allowing the obtention of a homogeneous composition.

Is a further object of the present invention the composition above-mentioned wherein the recovery of n-3 PUFA after 3 months at 40° C. is at least 94%, after 3 months, at 30° C. is at least 96%, after 3 months at 25° C. is at least 98% and after 3 months at 5° C. is at least 99% by weight;

Is a further object of the present invention the composition above-mentioned wherein the recovery of resveratrol after 3 months at 40° C. is at least 85%, after 3 months at 30° C. is at least 94%, after 3 months at 25° C. is at least 97% and after 3 months at 5° C. is at least 99% by weight.

In one embodiment of the present invention the omega-3 polyunsaturated fatty acids (n-3 PUFA) are selected from the group consisting of eicosapentaenoic acid (EPA), docosahexaenoic acid (DHA) or their alkyl esters, and mixtures thereof; and the alkyl ester of omega-3 polyunsaturated fatty acids (n-3 PUFA) are selected from the group consisting of ethyl, methyl, and propyl esters.

In a further embodiment of the present invention the omega-3 polyunsaturated fatty acids (n-3 PUFA) are a mixture of fatty acids having a content in EPA and DHA comprised between 75% and 95% by weight, preferably at least 85%, on the total fatty acids weight, and wherein the total content of n-3 PUFA is at least 90% by weight on the total fatty acids weight; and the ratio between eicosapentaenoic acid and docosahexaenoic acid is comprised between 0.5 and 2;

In another embodiment of the present invention the omega-3 polyunsaturated fatty acids (n-3 PUFA) are a mixture of ethyl esters of EPA and DHA in a ratio comprised between 0.9 and 1.5 and the content of EPA ethyl ester is comprised between 40 and 51% and the content of DHA ethyl ester is comprised between 34 and 45% by weight on the total fatty acids weight;

It is a further object of the present invention a composition which comprises:
(1) a solvent system consisting of:
omega-3 polyunsaturated fatty acid or alkyl esters thereof;
an ionic emulsifier selected from the group consisting of deoiled phosphatidylcholine-enriched lecithin or deoiled phosphatidylcholine-enriched lecithin wherein said phosphatidylcholine is present in an amount greater than 92% or Epikuron™ 200; and
(2) resveratrol, or a natural extract containing resveratrol;
in which resveratrol is completely dissolved in the solvent system allowing the obtention of a homogeneous composition, in the form of dietary or nutritional supplement, or medicament for oral administration.

In a further embodiment of the present invention in the composition above-mentioned the omega-3 polyunsaturated fatty acids (n-3 PUFA) are in an amount comprised between 0.5 and 1.0 g, preferably between 0.8 and 0.9 g, more preferably 0.9 g;

According to a further embodiment of the present invention the above-mentioned composition, can further comprise one or more vitamins, minerals, coenzymes, antioxidants and/or plant extracts.

According to a further embodiment of the present invention the above-mentioned composition, can further comprise at least one pharmaceutically acceptable vehicle or excipient.

It is a further object of the present invention the composition above-mentioned, characterized in that it is encapsulated by soft gelatin capsules, optionally having an enteric coating, for oral administration.

It is a further object of the present invention the composition above-mentioned, for use in preventing or treating cardiovascular diseases due to lipid metabolism disorders and/or increased platelets aggregation; and/or damages due to free radicals selected from the group consisting of atherosclerosis, cancer, inflammatory joint disease, asthma, diabetes, senile dementia and degenerative eye disease; and/or viral diseases.

It is a further object of the present invention the composition above mentioned, optionally further comprising 2-(2-ethoxyethoxy)ethanol.

The term "significant amount", according to the present invention means that an amount of resveratrol greater than or equal to 5 mg for 1 ml of solvent system is completely solubilized.

The term "homogeneous", according to the present invention means that there is no separation of phase, there is no particle suspended, there is no solid precipitate, and the solute (resveratrol) is completely dissolved in the solvent system.

It is a further object of the present invention a method for the preparation of the composition of the invention which comprises: preparing a solvent system solution consisting of a deoiled phosphatidylcholine-enriched lecithin and n-3 PUFA; and adding to this solvent system solution resveratrol; deriving in a "homogeneous" solution in which resveratrol is completely dissolved is obtained as exemplified in the experimental section.

The composition according to the invention can also comprise other useful elements, without this substantially impairing the activity. A non-limiting examples of useful elements according to the present invention comprise one or more vitamins, minerals, coenzymes, antioxidants and/or plant extracts.

A further object of the present invention is a composition containing the above-mentioned elements, optionally in a mixture with one or more pharmaceutically acceptable vehicles and/or excipients.

The pharmaceutical composition suitable for use according to the present invention generally comprises at least one pharmaceutically acceptable vehicle and/or one diluent and/or one surfactant and/or one thickener and/or one binder and/or one lubricant and/or one aromatizer and/or one colorant and/or one stabilizer and the like, which can easily be selected by the expert of the art.

The compositions of the invention, together with a conventionally employed adjuvant, carrier, diluent or excipient may be placed into the form of pharmaceutical compositions and unit dosages thereof, and such form may be employed as solids, such as tablets or filled capsules; or liquids such as solutions, suspensions, emulsions, elixirs, or capsules filled with the same, all for oral use. The compositions for oral administration may take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

Liquid forms suitable for oral administration may include a suitable aqueous or non-aqueous vehicle with buffers, suspending and dispensing agents, colorants, flavours and the like.

The above described components for orally administered are merely representative. Further materials as well as processing techniques and the like are set out in Part 5 of Remington's Pharmaceutical Sciences, 20th Edition, 2000, Merck Publishing Company, Easton, Pa., which is incorporated herein by reference.

The composition according to the present invention can also be formulated as a food supplement or dietary supplement, which constitutes a further object of the invention. The composition according to the present invention comprises active ingredients which are known in the art and already used in clinical practice. Therefore, they are very easy to procure, inasmuch as they are products which have been on the market for some time and are of a grade suitable for human or animal administration.

Resveratrol (3,5,4'-trihydroxy-trans-stilbene) is a stilbenoid, a type of natural phenol, and a phytoalexin produced naturally by several plants when under attack by pathogens such as bacteria or fungi.

The term "omega-3 polyunsaturated fatty acids" (here abbreviated as "n-3 PUFA") relates to a family of long-chain polyunsaturated fatty acids, generally $C_{16}$-$C_{24}$, in particular those having a $C_{20}$-$C_{22}$ chain, that have in common a carbon-carbon double bond in the n-3 position, i.e. the third bond from the methyl end of the fatty acid. Examples of the most common omega-3 polyunsaturated fatty acids found in nature are reported in the Table below together with their assigned names.

| Common name | Lipid name | Chemical name |
|---|---|---|
| Roughanic acid | 16:3 (n-3) | all-cis-7,10,13-hexadecatrienoic acid |
| α-Linolenic acid (ALA) | 18:3 (n-3) | all-cis-9,12,15-octadecatrienoic acid |
| Stearidonic acid (STD) | 18:4 (n-3) | all-cis-6,9,12,15-octadecatetraenoic acid |
| Eicosatrienoic acid (ETE) | 20:3 (n-3) | all-cis-11,14,17-eicosatrienoic acid |
| Eicosatetraenoic acid (ETA) | 20:4 (n-3) | all-cis-8,11,14,17-eicosatetraenoic acid |
| Eicosapentaenoic acid (EPA) | 20:5 (n-3) | all-cis-5,8,11,14,17-eicosapentaenoic acid |
| Docosapentaenoic acid (DPA), Clupanodonic acid | 22:5 (n-3) | all-cis-7,10,13,16,19-docosapentaenoic acid |
| Docosahexaenoic acid (DHA) | 22:6 (n-3) | all-cis-4,7,10,13,16,19-docosahexaenoic acid |
| Tetracosapentaenoic acid | 24:5 (n-3) | all-cis-9,12,15,18,21-Tetracosapentaenoic acid |
| Tetracosahexaenoic acid (Nisinic acid) | 24:6 (n-3) | all-cis-6,9,12,15,18,21-Tetracosahexaenoic acid |

The ones most preferred are all-cis-5,8,11,14,17-eicosapentaenoic acid (EPA) and all-cis-4,7,10,13,16,19-docosahexaenoic acid (DHA).

Preferably the n-3 PUFA according to the invention is a mixture of fatty acids having a high content in EPA and DHA, for example with a content in EPA and DHA higher than 25% by weight, preferably from about 30% to about 100% by weight, in particular about between 75% and 95%, and more preferably at least 85% by weight based on the total fatty acid weight. Preferably the total content of n-3

PUFA according to the invention is a mixture of fatty acids having at least 90% of n-3 PUFA by weight based on the total fatty acid weight.

The terms "PUFA" and "n-3 PUFA", as used here, are intended to encompass their corresponding $C_1$-$C_3$ alkyl esters, preferably ethyl esters, and/or their salts with pharmaceutically acceptable bases such as sodium hydroxide, lysine, arginine or aminoalcohols such as choline. The ethyl esters are the most widely used and preferred according to the invention.

The composition of the invention is administered orally, in particular in the form of soft gelatin capsules. For oral use, the unit dose generally comprises 100-1000 mg of polyunsaturated fatty acids of the omega-3 series, preferably 500-1000 mg or 300-500 mg, the total dose being usually around 0.1-3.0 g per day, preferably 0.3-2.0 g per day, most preferably 1.0 g per day.

Specific drugs containing n-3 PUFA that meet the above specifications, as active ingredient and that can be used according to the present invention, are already available on the market.

This amount of product may be administered in the form of several daily divided doses or preferably as a single dose, in order to reach the desired blood level. Of course, the clinician may vary the amount of product (or mixture with another therapeutic agent) to be administered, according to the patient's conditions, age and weight.

Other types of formulation for oral administration are also suitable for the purposes of the invention; for example hard capsules or tablets, in which the polyunsaturated fatty acids are adsorbed on solid supports. It is also possible to use emulsions, granulates in dispersing excipients, syrups, droplets, etc., and other forms of administration able to ensure systemic absorption of the drug, such as sterile solutions or emulsions and the like, suitable for parenteral use, as evaluated by the expert of the art, on the basis of the severity of the pathology.

Those compositions illustrated in the European Pharmacopoiea 2000 (EuPh. 2000), containing quantities greater than or equal to 90 wt % of omega-3 polyunsaturated fatty acid (n-3 PUFA) polyunsaturated fatty acid ethyl esters, of which an amount greater than or equal to 80 wt % is represented by of mixtures of EPA and DHA ethyl esters and a are also suitable for the purposes of the present invention.

The most preferred ratio between EPA and DHA is about 0.6-1.1/1.3-1.8; in particular is comprised between 0.9 and 1.5.

Preferably the content of EPA (as ethyl ester) is comprised between 40 and 51% by weight and the content of DHA (as ethyl ester) is comprises between 34 and 45% by weight on the total fatty acids weight.

Phosphatidylcholines (PC) are a class of phospholipids that incorporate choline as a head group. They are a major component of biological membranes and can be easily obtained from a variety of readily available sources such as egg yolk or soy beans from which they are mechanically extracted or chemically extracted using hexane. They are also a member of the lecithin group of yellow-brownish fatty substances occurring in animal and plant tissues.

For the purpose of the present invention the ionic emulsifier is a deoiled and purified soy lecithin enriched with at least 92% of phosphatidylcholine such as Epikuron™ 200. It is known in the art that soy lecithin is endowed with an anticholesterolemic activity. Therefore another advantage of the present invention is that said soy lecithin in combination with n-3 PUFA and resveratrol will increase, in an additive manner, the pharmacological activity of the composition of the invention.

A non-limiting example of the lecithin according to the present invention is the one sold under the trade name "Epikuron™ 200".

In another embodiment of the present invention the composition has a unitary form, in which the active ingredients are present in a single pharmaceutical form, particularly adsorbed on an inert support. The compositions according to the present invention optionally contain, along with the active ingredient, at least one pharmaceutically acceptable vehicle or excipient.

In order to demonstrate its substantial advantages and unexpected effects, the present invention is carried out according to following examples, but not limited to these examples.

DETAILED DESCRIPTION OF THE INVENTION

Examples

Materials and Methods:

For the purpose of the present invention the following materials have been used:
 the omega-3 polyunsaturated fatty acids (n-3 PUFA) are a mixture of ethyl esters of polyunsaturated fatty acids with a content in EPA and DHA greater than 85%, in a ratio EPA/DHA comprised between 0.9 and 1.5, and is a product provided by SPA (Pronova, Norway);
 the resveratrol is furnished by Royalmount Pharma, Montreal, Canada;
 the mixture of glyceryl and polyethylene glycol esters, also known under the trade name Labrasol® is furnished by GATTEFOSSE' ITALIA, S.r.l (Milan, Italy);
 the propylene glycol monolaurate, also known under the trade name Lauroglycol 90™, is furnished by GATTEFOSSE' ITALIA, S.r.l (Milan, Italy).
 the polyoxyethylenglyceroltrihydroxystearate, also known under the trade name Cremophor RH 40®, is furnished by BASF Italia Srl;
 the polyoxyethylene(20)sorbitan monooleate, also known under the trade name Tween 80®, is furnished by Sigma-Aldrich; and
 the deoiled phosphatidylcholine-enriched lecithin, also known under the trade name Epikuron™ 200 is furnished by Cargill;

HPLC Analysis:

The same method was applied to all the formulations in which the solution was clear at a first sight. The solution to be analyzed was left under mechanical centrifugation and then the supernatant was separated trough filtration on PTFE (polytetrafluoroethylene) filter (size pore 0.22 μm) and analyzed by HPLC, using a Column Intersil ODS-3 4.6×250 mm, a solution of $CH_3CN/H_2O$ 70/30+0.1% of $CF_3COOH$ as eluent, a flow of 1 ml/min and a UV/VIS Detector ($\lambda$=311 nm).

Stability Analysis:

The formulations were divided into 4 groups; each group being respectively left for 3 months: at 5° C. at 60% RH (relative humidity), at 25° C. at 60% RH, at 30° C. at 60% RH and at 40° C. at 70% RH.

A 10 ml sample was then taken and a suitable amount was analysed by HPLC with the method described above. The percent detected amount of EPA, DHA and resveratrol are expressed as % of weight.

Formulation 1

500 mg of polyoxyethylene(20)sorbitan monooleate (Tween 80®) were added to 4.5 g of n-3 PUFA and the solution was left under mechanical stirring at 600 rpm for 3 hours at 22° C. at 60% RH; an opalescent solution was observed. A sample of 2 ml was taken out and 50 mg of resveratrol were added to it; the mixture obtained was left again under mechanical stirring at 600 rpm for 24 hours at 22° C. The solution was then analyzed by HPLC with the method described above.

Formulation 2

500 mg of Polyoxyethylenglyceroltrihydroxystearate (Cremophor RH 40®) were added to 4.5 g of n-3 PUFA and the solution was left under mechanical stirring at 600 rpm for 3 hours at 22° C. at 60% RH; an opalescent solution was observed. A sample of 2 ml was taken out and 50 mg of resveratrol were added to it; the mixture obtained was left again under mechanical stirring at 600 rpm for 24 hours at 22° C. The solution was then analyzed by HPLC with the method described above.

Formulation 3

500 mg of mixture of glyceryl and polyethylene glycol esters (Labrasol®) were added to 4.5 g of n-3 PUFA and the solution was left under mechanical stirring at 600 rpm for 3 hours at 22° C. and 60% RH; an opalescent solution was observed. A sample of 2 ml was taken out and 50 mg of resveratrol were added to it; the mixture obtained was left again under mechanical stirring at 600 rpm for 24 hours at 22° C. The solution was then analyzed by HPLC with the method described above.

Formulation 4

500 mg of mixture of propylene glycol monolaurate (Lauroglycol 90™) were added to 4.5 g of n-3 PUFA and the solution was left under mechanical stirring at 600 rpm for 3 hours at 22° C. and 60% RH (relative humidity); a clear solution was observed. A sample of 2 ml was taken out and 50 mg of resveratrol were added to it; the solution and the mixture obtained was left again under mechanical stirring at 600 rpm for 24 hours at 22° C. The solution was then analyzed by HPLC with the method described above.

Formulation 5

500 mg of sodium docusate were added to 4.5 g of n-3 PUFA and the solution was left under mechanical stirring at 600 rpm for 18 hours at 22° C. e 60% RH; a clear yellow solution was observed. A sample of 2 ml was taken out and 50 mg of resveratrol were added to it; the solution and the mixture obtained was left again under mechanical stirring at 600 rpm for 24 hours at 22° C. The solution was then analyzed by HPLC with the method described above.

Formulation 6

500 mg of g deoiled phosphatidylcholine-enriched lecithin (Epikuron™ 200) were added to 4.5 g of n-3 PUFA and the solution was left under mechanical stirring at 600 rpm for 18 hours at 22° C. at 60% RH. A clear yellow solution was observed. A sample of 2 ml was taken out and 50 mg of resveratrol were added to it; the mixture obtained was left again under mechanical stirring at 600 rpm for 24 hours at 22° C. The solution was then analyzed by HPLC with the method described above.

For this formulation stability test were also performed. The percentage amount of EPA, DHA and resveratrol was initially measured and the solution was then divided into 4 samples being left each for 6 months at a different temperature. The samples was then analysed by HPLC. The results are reported in the following table; at least 85% of the resveratrol in the composition at an initial measurement time was maintained after 6 month at 40° C. at 70% of RH.

TABLE 1

| Temperature (° C.) | Recovery EPA (%) | Recovery DHA (%) | Recovery Resveratrol (%) |
|---|---|---|---|
| 5 | 99 | 99 | 99 |
| 25 | 98 | 98 | 97 |
| 30 | 97 | 96 | 94 |
| 40 | 95 | 94 | 85 |

For an easier reference the results obtained for all previous formulations, which represents the maximum solubility of resveratrol in omega-3 polyunsaturated fatty acids (n-3 PUFA) with the addition of the emulsifiers, are summarized in Table 2.

TABLE 2

| Formul. No. | Oil | Emulsifier | Maximum Resveratrol Solubility (mg/ml) |
|---|---|---|---|
| Control | n-3 PUFA | None | 0.25 |
| 1 | n-3 PUFA | 10% w/w Tween 80 ® | 1.98 |
| 2 | n-3 PUFA | 10% w/w Cremophor RH 40 ® | 2.47 |
| 3 | n-3 PUFA | 10% w/w Labrasol ® | 2.63 |
| 4 | n-3 PUFA | 10% w/w Lauroglycol 90 ™ | 1.77 |
| 5 | n-3 PUFA | 10% w/w Sodium docusate | 0.84 |
| 6 | n-3 PUFA | 10% w/w Epikuron ™ 200 | 18.00 |

Discussion of the Results:

The experimental data reported in this application show that the solvent system used allows to achieve complete solubilization of a significant amount of resveratrol, which is otherwise poorly soluble in n-3 PUFA.

The solubility of resveratrol in PUFA alone (0.25 mg/ml), as can be seen from the results of Table 2, is increased of 72 times, reaching a maximum of 18 mg/ml in the formulation with Epikuron™ 200.

The stability demonstrated by formulation 6 makes the solution of resveratrol in omega-3 fatty acids very useful for an easy preparation of compositions for oral administration, for use in the prevention or treatment of cardiovascular diseases due to lipid metabolism disorders and/or increased platelets aggregation, damages due to free radicals and/or viral diseases.

The composition comprising resveratrol and the solvent system consisting of omega-3 fatty acids and Epikuron™ 200 could also be easy used for further solubilizing and delivering other useful elements.

Furthermore, the process of preparation of the present compositions is simple and particularly suitable for industrial applicability.

The invention claimed is:

1. A composition which comprises:
    a) a solvent system comprising an omega-3 polyunsaturated fatty acid or alkyl esters thereof, and an ionic emulsifier which is a deoiled soy lecithin enriched with at least 92% of phosphatidyl choline; and
    b) resveratrol, or a natural extract containing resveratrol; wherein the composition is characterized in that resveratrol is completely dissolved, and the composition is homogeneous.

2. The composition of claim 1, wherein the omega-3 polyunsaturated fatty acid (n-3 PUFA) is selected from the group consisting of eicosapentaenoic acid (EPA), docosahexaenoic acid (DHA) and mixtures thereof.

3. The composition of claim 2, wherein the n-3 PUFA is a mixture of eicosapentaenoic and docosahexaenoic acids, and the ratio between eicosapentaenoic acid and docosahexaenoic acid is comprised between 0.5 and 2.

4. The composition of claim 1, wherein the n-3 PUFA is a mixture of fatty acids, said n-3 PUFA having a content in EPA and DHA comprised between 75% and 95% by weight of the total fatty acids weight.

5. The composition of claim 1, wherein the n-3 PUFA is a mixture of ethyl esters of EPA and DHA in a ratio between 0.9 and 1.5 and the content of EPA ethyl ester is between 40 and 51% and the content of DHA ethyl ester is between 34 and 45% by weight of the total fatty acids weight.

6. The composition of claim 1, wherein the alkyl ester of n-3 PUFA is selected from ethyl, methyl or propyl esters or mixtures thereof.

7. The composition of claim 1, wherein the n-3 PUFA is in an amount between 0.5 and 1.0 g.

8. The composition of claim 1, wherein the recovery of n-3 PUFA after 3 months at 40° C. is at least 94% by weight.

9. The composition of claim 1, wherein the recovery of resveratrol after 3 months at 40° C. is at least 85% by weight.

10. The composition of claim 1, wherein the composition is formulated as a dietary supplement or for oral administration.

11. The composition of claim 1, further comprising one or more vitamins, minerals, coenzymes, antioxidants and/or plant extracts.

12. The composition of claim 1, further comprising at least one pharmaceutically acceptable vehicle or excipient.

13. The composition of claim 1, wherein the composition is encapsulated by soft gelatin capsules, optionally having an enteric coating, for oral administration.

14. The composition of claim 8, wherein the recovery of n-3 PUFA after 3 months:
(i) at 30° C. is at least 96% by weight,
(ii) at 25° C. is at least 98% by weight, or
(iii) at 5° C. is at least 99% by weight.

15. The composition of claim 9, wherein the recovery of resveratrol after 3 months is:
(i) at 30° C. is at least 94% by weight,
(ii) at 25° C. is at least 97% by weight, or
(iii) at 5° C. is at least 99% by weight.

16. The composition of claim 4, wherein the total content of n-3 PUFA is at least 90% by weight of the total fatty acids weight.

* * * * *